US011436786B2
US 11,436,786 B2

(12) United States Patent
Inoue et al.

(10) Patent No.: US 11,436,786 B2
(45) Date of Patent: Sep. 6, 2022

(54) MEDICAL DIAGNOSTIC IMAGING SUPPORT SYSTEM, MEDICAL IMAGE PROCESSING DEVICE, AND MEDICAL IMAGE PROCESSING METHOD

(71) Applicant: Hitachi, Ltd., Tokyo (JP)

(72) Inventors: Atsushi Inoue, Tokyo (JP); Takashi Shirahata, Tokyo (JP); Takayuki Kadomura, Tokyo (JP)

(73) Assignee: FUJIFILM Healthcare Corporation, Chiba (JP)

( * ) Notice: Subject to any disclaimer, the term of this patent is extended or adjusted under 35 U.S.C. 154(b) by 180 days.

(21) Appl. No.: 16/901,306

(22) Filed: Jun. 15, 2020

(65) Prior Publication Data
US 2021/0166465 A1    Jun. 3, 2021

(30) Foreign Application Priority Data
Nov. 29, 2019   (JP) .............................. JP2019-216057

(51) Int. Cl.
*G06K 9/00* (2022.01)
*G06T 15/08* (2011.01)
(Continued)

(52) U.S. Cl.
CPC .............. *G06T 15/08* (2013.01); *A61B 6/032* (2013.01); *A61B 6/5217* (2013.01); *A61B 6/54* (2013.01);
(Continued)

(58) Field of Classification Search
None
See application file for complete search history.

(56) References Cited

U.S. PATENT DOCUMENTS 10,354,360 B2 *   7/2019   Sakamoto ................ G06T 3/40
2005/0037406 A1 * 2/2005   De La Torre-Bueno ....................
                                                    G06T 5/50
                                                    435/6.12
(Continued)

FOREIGN PATENT DOCUMENTS

EP          3301649 A1      4/2018
JP      2018-061771 A       4/2018

OTHER PUBLICATIONS

Extended European Search Report, dated Oct. 15, 2020, for European Application No. 20180171.9.

*Primary Examiner* — Oneal R Mistry
(74) *Attorney, Agent, or Firm* — Baker Botts L.L.P.

(57) ABSTRACT

To reduce time required for establishing diagnosis of a lesion candidate, a diagnostic imaging support system including a medical image shooting device for shooting an image of a subject and a medical image processing device for processing the medical image, the system including: a projection data acquisition part for acquiring projection data of the subject; a reconstruction part for reconstructing the medical image based on the projection data; an acquisition part for acquiring lesion candidate data which is data on lesion candidates detected from the medical image; a reconstruction condition decision part for deciding, on the basis of the lesion candidate data, a reconstruction condition for a magnified reconstruction image which includes the lesion candidates and is more magnified than the medical image; a magnification reconstruction part for reconstructing the magnified reconstruction image by using the reconstruction condition; and a display part for displaying the magnified reconstruction image.

26 Claims, 12 Drawing Sheets

(51) Int. Cl.
- *G06T 7/62* (2017.01)
- *G16H 70/60* (2018.01)
- *G16H 15/00* (2018.01)
- *G16H 50/30* (2018.01)
- *G16H 50/20* (2018.01)
- *G16H 30/40* (2018.01)
- *G06F 16/54* (2019.01)
- *A61B 6/03* (2006.01)
- *A61B 6/00* (2006.01)
- *G06T 7/00* (2017.01)

(52) U.S. Cl.
CPC .......... *G06F 16/54* (2019.01); *G06T 7/0012* (2013.01); *G06T 7/62* (2017.01); *G16H 15/00* (2018.01); *G16H 30/40* (2018.01); *G16H 50/20* (2018.01); *G16H 50/30* (2018.01); *G16H 70/60* (2018.01); *G06T 2207/10081* (2013.01); *G06T 2207/20081* (2013.01); *G06T 2207/30096* (2013.01); *G06T 2210/41* (2013.01)

(56) References Cited

U.S. PATENT DOCUMENTS

| | | | |
|---|---|---|---|
| 2007/0027733 A1* | 2/2007 | Bolle | G06Q 10/0639 705/7.13 |
| 2013/0222415 A1* | 8/2013 | Vilsmeier | G06T 15/503 345/619 |
| 2013/0308839 A1* | 11/2013 | Taylor | G16H 30/20 382/128 |
| 2015/0036903 A1 | 2/2015 | Jerebko | |
| 2016/0058288 A1* | 3/2016 | DeBernardis | A61B 5/0075 600/477 |
| 2019/0236763 A1* | 8/2019 | Chan | A61B 6/032 |
| 2020/0310100 A1* | 10/2020 | Ozcan | G03H 1/0443 |
| 2021/0343008 A1* | 11/2021 | Okuda | G06T 7/11 |

* cited by examiner

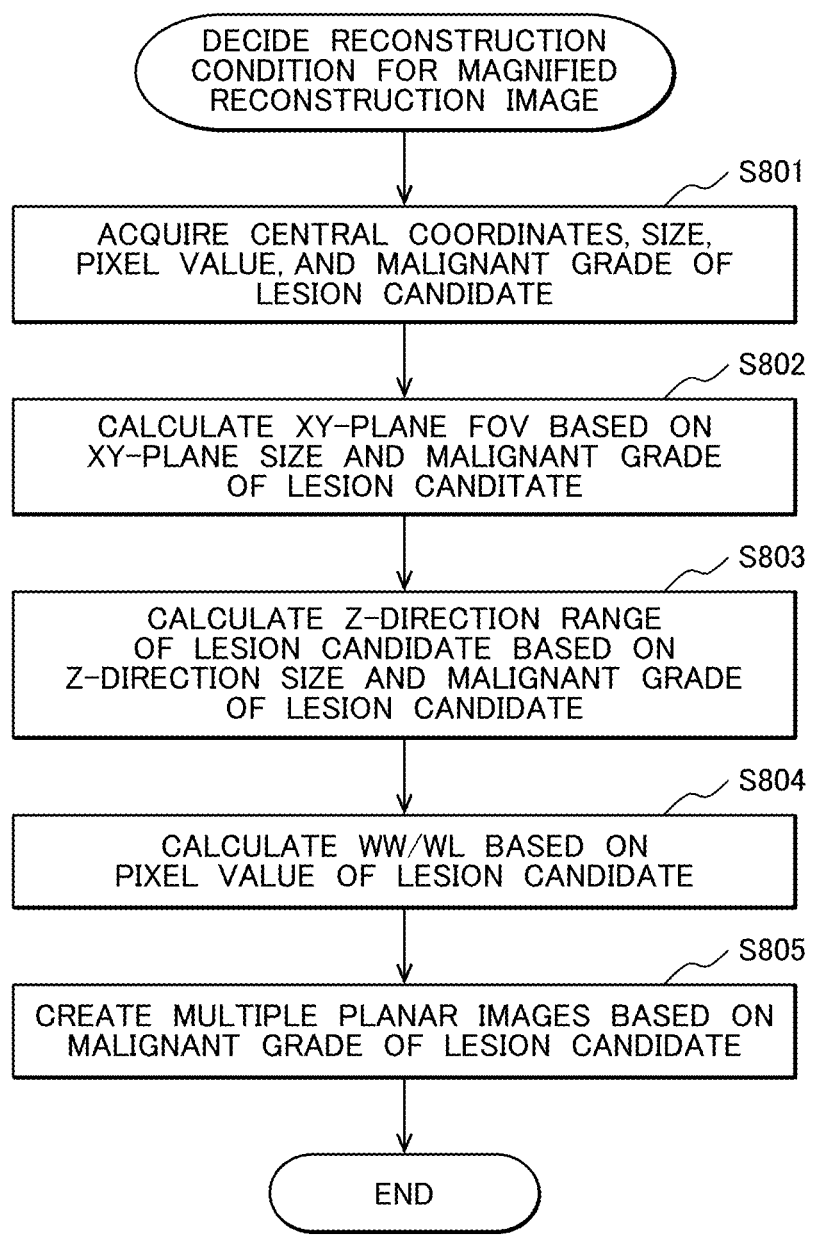

| MALIGNANT GRADE R OF LESION CANDIDATE | ANGLES θ OF MULTILPLE PLANAR IMAGES |
|---|---|
| 0.0 < R ≦ 0.2 | 0°、90° |
| 0.2 < R ≦ 0.4 | 0°、45°、90°、135° |
| 0.4 < R ≦ 0.6 | 0°、30°、60°、90°、120°、150° |
| 0.6 < R ≦ 0.8 | 0°、45°、90°、135° |
| 0.8 < R ≦ 1.0 | 0°、90° |

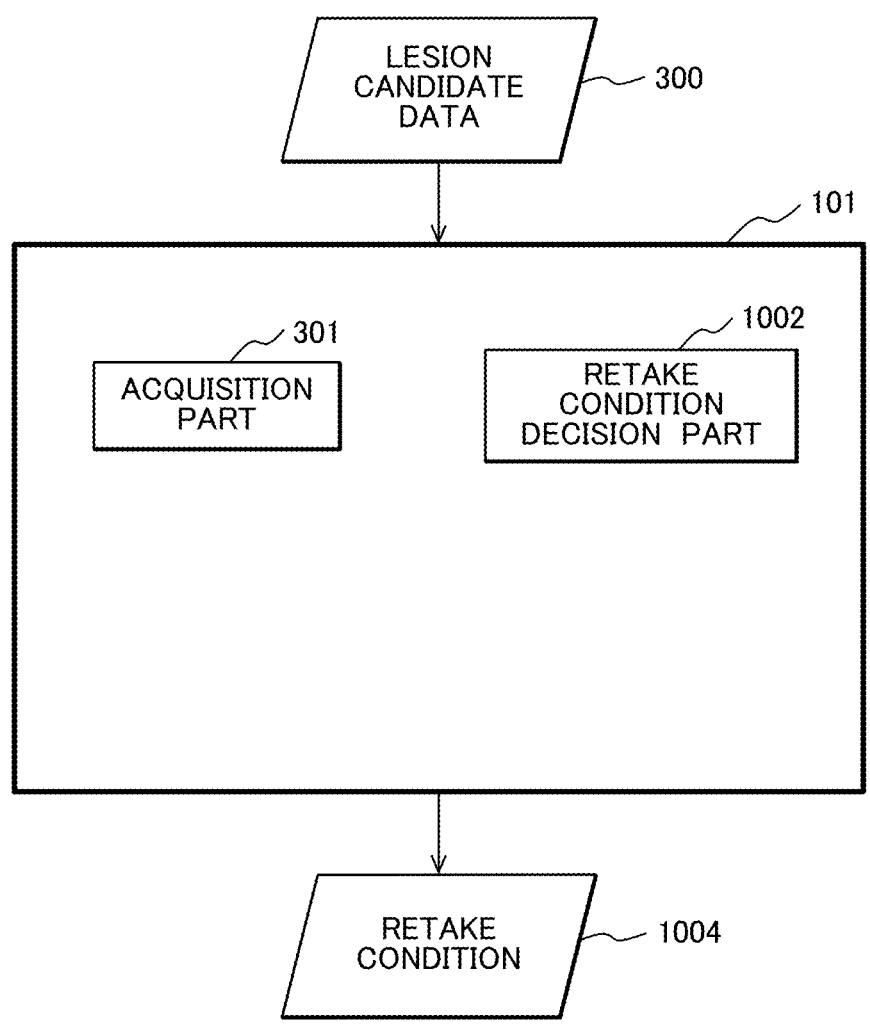

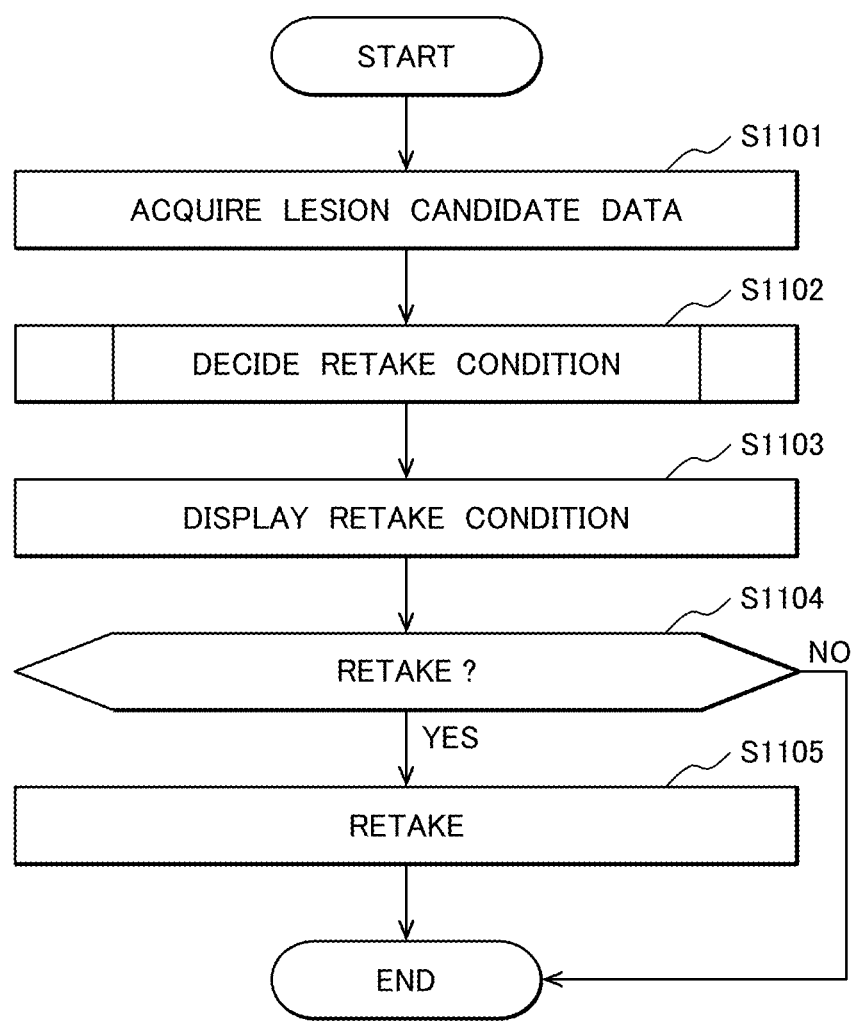

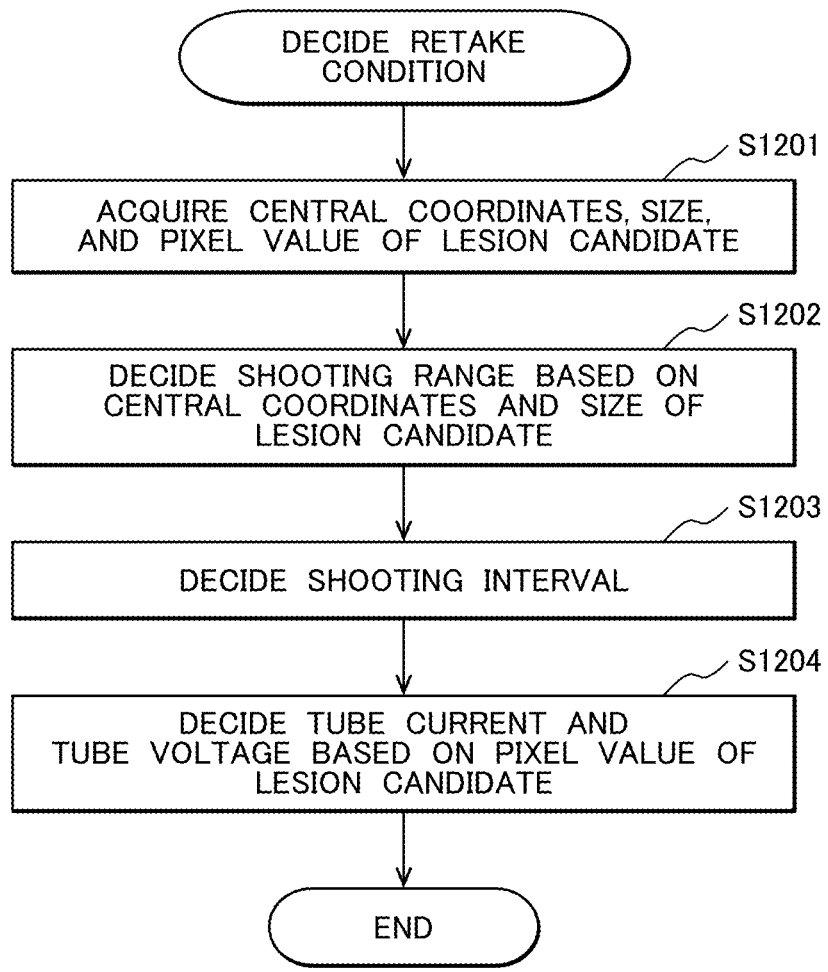

MEDICAL DIAGNOSTIC IMAGING SUPPORT SYSTEM, MEDICAL IMAGE PROCESSING DEVICE, AND MEDICAL IMAGE PROCESSING METHOD

CLAIM OF PRIORITY

The present application claims priority from Japanese Patent Application JP 2019-216057 filed on Nov. 29, 2019, the content of which are hereby incorporated by references into this application.

BACKGROUND OF THE INVENTION

The present invention relates to a medical diagnostic imaging support system including a medical image shooting device for shooting medical images and a medical image processing device for processing the medical image, as well as to a medical image processing device and a medical image processing method. More particularly, the present invention relates to the processing of the medical images handled by the medical diagnostic imaging support system.

BACKGROUND ART

With technical advancement in performance of the medical image shooting device typified by X-ray CT (Computed Tomography) apparatus, a larger volume of medical images is acquired, which imposes an increasing stress on medical image interpretation specialists.

In order to reduce stress on the medical image interpretation specialists, a medical diagnostic imaging support system, a so-called CAD (Computer Aided Detection) system, in which a computer supports imaging diagnosis by detecting and showing a lesion candidate from medical images has been disclosed in Japanese Patent Application Laid-Open No. 2018-61771.

SUMMARY OF THE INVENTION

Unfortunately, Japanese Patent Application Laid-Open No. 2018-61771 does not go beyond presenting the lesion candidate detected by the CAD. There may be a case where a medical image interpretation specialist must work long hours to determine whether the lesion candidate is a lesion or not. Specifically, a simply magnified medical image is not enough for the medical image interpretation specialist to establish the diagnosis of the lesion candidate. The medical image interpretation specialist needs more specific data or need to ask a medical radiographer to create a magnified reconstruction image related to the lesion candidate, for example. Thus, it takes long hours to establish the diagnosis.

It is, accordingly, an object of the present invention to provide a diagnostic imaging support system adapted to reduce time required for establishing the diagnosis of the lesion candidate, as well as a medical image processing device and a medical image processing method.

According to an aspect of the present invention for achieving the above object, a diagnostic imaging support system including a medical image shooting device for shooting a medical image of a subject and a medical image processing device for processing the medical image, includes: a projection data acquisition part for acquiring projection data of the subject; a reconstruction part for reconstructing the medical image based on the projection data; an acquisition part for acquiring lesion candidate data which is data of lesion candidates detected from the medical image; a reconstruction condition decision part for deciding, on the basis of the lesion candidate data, a reconstruction condition for a magnified reconstruction image which includes the lesion candidates and is more magnified than the medical image; a magnification reconstruction part for reconstructing the magnified reconstruction image by using the reconstruction condition; and a display part for displaying the magnified reconstruction image.

According to another aspect of the present invention, a medical image processing device for processing a medical image, includes: an acquisition part for acquiring lesion candidate data which is data of lesion candidates detected from the medical image; a reconstruction condition decision part for deciding, on the basis of the lesion candidate data, a reconstruction condition for a magnified reconstruction image which includes the lesion candidates and is more magnified than the medical image; a magnification reconstruction part for reconstructing the magnified reconstruction image by using the reconstruction condition; and a display part for displaying the magnified reconstruction image.

According to another aspect of the present invention, a medical image processing method for processing a medical image includes: an acquisition step of acquiring lesion candidate data which is data of lesion candidates detected from the medical image; a reconstruction condition decision step of deciding, on the basis of the lesion candidate data, a reconstruction condition for a magnified reconstruction image which includes the lesion candidates and is more magnified than the medical image; a magnification reconstruction step of reconstructing the magnified reconstruction image by using the reconstruction condition; and a display step of displaying the magnified reconstruction image.

According to the present invention, the diagnostic imaging support system adapted to reduce time required for establishing the diagnosis of the lesion candidate, as well as the related medical image processing device and medical image processing method can be provided.

BRIEF DESCRIPTION OF THE DRAWINGS

FIG. 8 is a flow chart showing an exemplary flow of processing of deciding a reconstruction condition for a magnified reconstruction image according to a second embodiment hereof;

FIG. 10 is a functional block diagram of a third embodiment hereof;

FIG. 11 is a flow chart showing an exemplary flow of processing of the third embodiment; and FIG. 12 is a flow chart showing an exemplary flow of processing of deciding a retake condition according to the third embodiment.

DETAILED DESCRIPTION OF THE PREFERRED EMBODIMENTS

Figure 1:
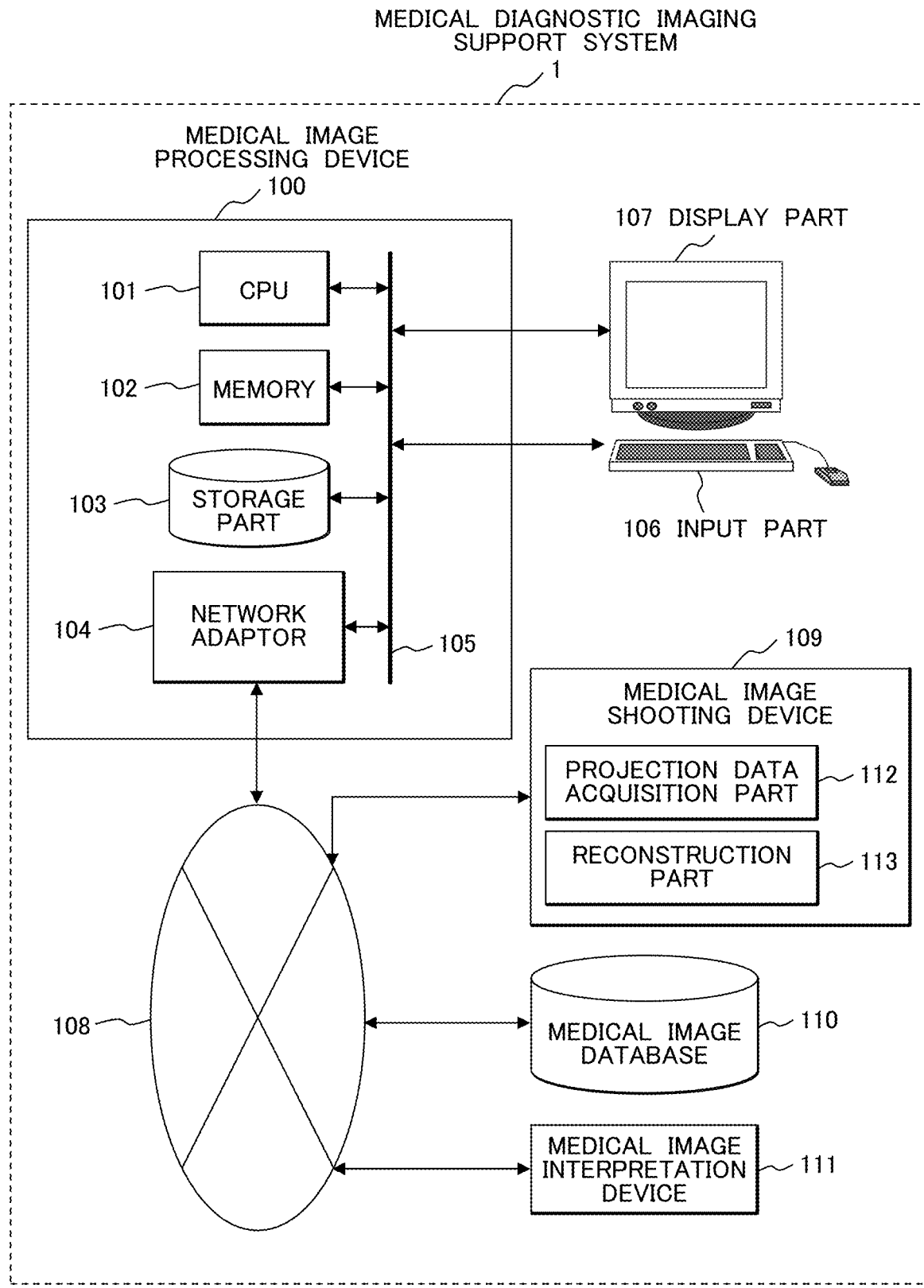
FIG. 1 is a hardware configuration diagram of a medical diagnostic imaging support system according to a first embodiment hereof.

A medical diagnostic imaging support system, a medical image processing device and a medical image processing method according to preferred embodiments of the present invention will hereinbelow be described with reference to the accompanying drawings. Throughout the following description and accompanying drawings, equal or similar reference numerals are assigned to equal or similar components which are explained only once in principle to avoid repetitions.

First Embodiment

A hardware configuration of a medical diagnostic imaging support system 1 of the embodiment is described with reference to FIG. 1. The medical diagnostic imaging support system 1 includes a medical image processing device 100, a medical image shooting device 109, a medical image database 110, and a medical image interpretation device 111 which are interconnected in a manner to be allowed to transmit or receive signals via a network 108.

The medical image processing device 100 is a so-called computer. Specifically, the medical image processing device 100 is constructed by interconnecting a CPU (Central Processing Unit) 101, a memory 102, a storage part 103, a network adapter 104, an input part 106, and a display part 107 by means of a bus 105 in a manner to be capable of transmitting or receiving signals. The phrase herein "in a manner to be capable of transmitting or receiving signals" means a state where signals can be electrically or optically delivered to each other or delivered from one side to the other regardless of whether it is by wire or by air.

The CPU 101 is a device which retrieves a system program and the like from the storage part 103 so as to control the operations of the individual components. The CPU 101 loads a program and data necessary for the execution of the program, which are stored in the storage part 103, in a memory 102 before carrying out the program. The storage part 103 is a device for storing programs to be executed by the CPU 101 and data necessary for the execution of the program. Specifically, the storage part is a recording device such as HDD (Hard Disk Drive) and SSD (Solid State Drive) or a device for reading/writing data or a program from/in a recording medium such as IC card, SD card, and DVD. A variety of data including data necessary for program execution is also transmitted or received over the network 108 such as LAN (Local Area Network) and the like. An ongoing status or the like of a program or arithmetic processing executed by the CPU 101 is stored in the memory 102.

The display part 107 is a device which displays the results of the program execution and the like. Specifically, the display part 107 is a liquid crystal display or the like. The input part 106 is an operation device via which an operator gives an operational instruction to the medical image processing device 100. Specifically, the input part 106 is a keyboard, mouse, and the like. The mouse may be another pointing device such as a track pad and track ball. In a case where the display part 107 is a touch panel, the touch panel also functions as the input part 106. The network adapter 104 is for connecting the medical image processing device 100 to the network 108 such as LAN, phone line and the Internet.

The medical image shooting device 109 is a device for acquiring a medical image such as tomographic image visualizing a morphology of a lesion area, and the like, as exemplified by an X-ray Computed Tomography scanner. The medical image shooting device 109 includes a projection data acquisition part 112 and a reconstruction part 113. The projection data acquisition part 112 is a device for acquiring projection data including projection images of a subject taken at various angles, as exemplified by a scanner which rotates an X-ray source and an X-ray detector around the subject. The reconstruction part 113 is a device for reconstructing a tomographic image based on the projection data. Specifically, the reconstruction part is a so-called computer. Each of the projection data acquisition part 112 and the reconstruction part 113 may be implemented by a dedicated hardware using ASIC (Application Specific Integrated Circuit), FPGA (Field-Programmable Gate Array), and the like installed in the medical image shooting device 109. Otherwise, the projection data acquisition part 112 and the reconstruction part 113 may each be implemented by a software operated on the CPU. A three-dimensional medical image is created by superimposing plural tomographic images on top of each other.

The medical image database 110 is a database system storing the medical images acquired by the medical image shooting device 109. The medical image is stored in the medical image database 110 along with DICOM (Digital Imaging and Communications in Medicine) including shooting conditions and the like of the medical images.

The medical image interpretation device 111 is a device equipped with a viewer function for interpretation of the medical images. Specifically, the device is a so-called computer. The medical image interpretation device 111 may also be integrated with the medical image processing device 100.

The medical image processing device 100 is a computer operative to detect, from the medical image, a lesion candidate which is a tissue likely to be a lesion, to determine a malignant grade of the detected lesion candidate or to identify an organ included in the medical image. A detection program for lesion candidate may be constructed by AI (Artificial Intelligence). The detection program may also be equipped with a machine learning function to collect leaning data including a collection of pairs of medical images and lesions.

Figure 2A:
FIG. 2A shows an exemplary medical image.
Figure 2B:
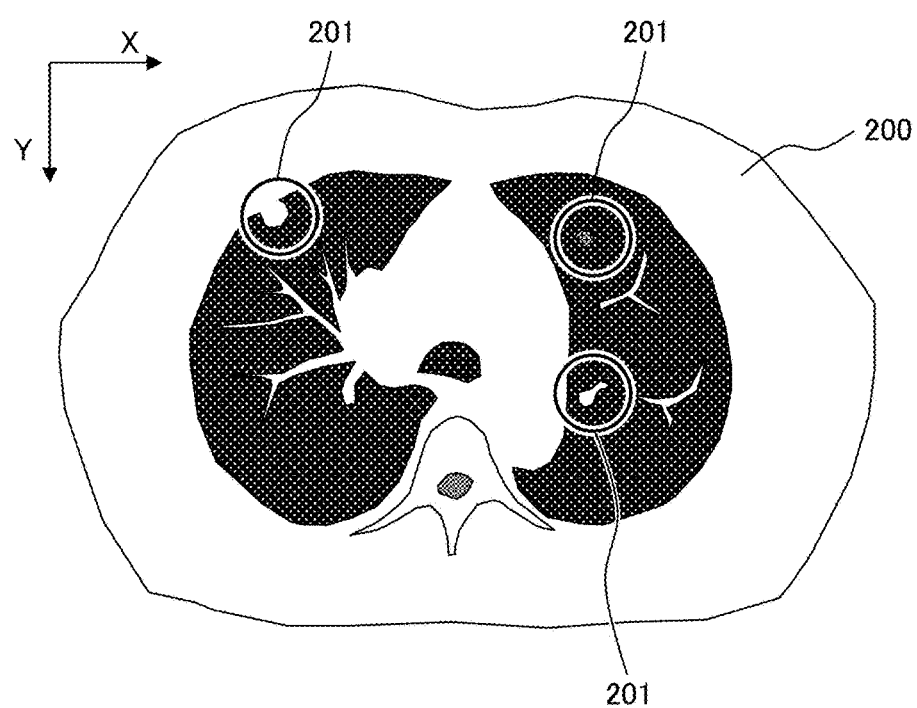
FIG. 2B shows exemplary lesion candidates.

Referring to FIG. 2, description is made on the medical image acquired by the medical image shooting device 109 and the lesion candidate detected by the medical image processing device 100. FIG. 2A shows a medical image or tomographic image 200 of a lung field taken by an X-ray CT device while FIG. 2B shows three lesion candidates 201 detected from the tomographic image 200. The tomographic image 200 is reconstructed on an XY plane and Z-direction perpendicular to the XY plane is a direction of body axis of the subject. The medical image interpretation specialist reads the tomographic image 200 of FIG. 2A and then, reads again the tomographic image 200 with reference to the lesion candidates 201 shown in FIG. 2B. Otherwise, the medical image interpretation specialist interprets the tomographic image while referring to the lesion candidates 201 shown in FIG. 2B. Either way, the medical image interpretation specialist reads the tomographic image 200 and gives a diagnosis with respect to the tomographic image 200 and the lesion candidates 201.

Figure 3:
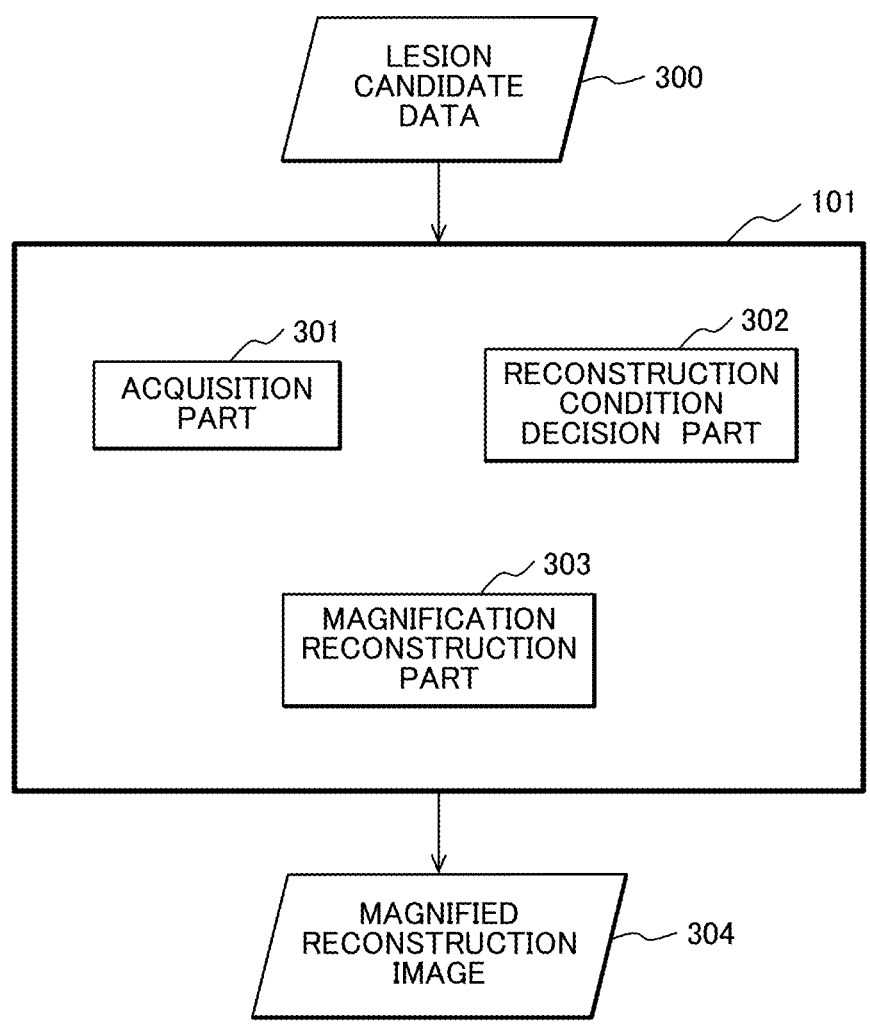
FIG. 3 is a functional block diagram of the first embodiment.

A functional block diagram of the medical image processing device 100 of the embodiment is described with reference to FIG. 3. It is noted that these functions may be implemented by a dedicated hardware using ASIC (Application Specific Integrated Circuit), FPGA (Field-Programmable Gate Array), and the like, or otherwise implemented by a software operated on the CPU 1. The following description is made on a case where the individual functions are implemented by software. The embodiment includes an acquisition part 301, a reconstruction condition decision part 302, and a magnification reconstruction part 303. The individual parts are described as below.

The acquisition part 301 acquires lesion candidate data 300 which is data on lesion candidates detected from the medical images by the medical image processing device 100. The lesion candidate data 300 includes, for example, three-dimensional coordinates, size, pixel value, malignant grade, and the like of the lesion candidate.

The reconstruction condition decision part 302 decides a reconstruction condition for a magnified reconstruction image 304 on the basis of the lesion candidate data 300. The magnified reconstruction image includes the lesion candidate and is more magnified than the medical image.

The magnification reconstruction part 303 reconstructs the magnified reconstruction image 304 by using the reconstruction condition decided by the reconstruction condition decision part 302. The magnified reconstruction image 304 thus reconstructed is displayed on the display part 107. Incidentally, the magnification reconstruction part 303 may be constructed by a computer other than the medical image processing device 100. Alternatively, the reconstruction part 113 of the medical image shooting device 109 may execute the magnification reconstruction.

An example of a processing flow of the embodiment is described with reference to FIG. 4.
(S401)
The projection data acquisition part 112 acquires projection data of the subject. The acquired projection data is transmitted to the reconstruction part 113. The projection data may also be stored in the medical image database 110 or the storage part 103.
(S402)
The reconstruction part 113 reconstructs a medical image based on the projection image acquired in S401. The reconstruction part 113 transmits the reconstructed image to the medical image processing device 100. The medical image may also be stored in the medical image database 110 or the storage part 103.
(S403)
The CPU 101 of the medical image processing device 100 detects a lesion candidate from the medical image reconstructed in S402. Next, the CPU 101 creates lesion candidate data 300 based on the detected lesion candidate and stores the resultant data in the memory 102.
(S404)
The acquisition part 301 acquires the lesion candidate data 300 from the memory 102.
(S405)
The reconstruction condition decision part 302 decides a reconstruction condition for magnified reconstruction image on the basis of the lesion candidate data 300 acquired in S404. The reconstruction condition includes field of view of the magnified reconstruction image, reconstruction interval, and thickness. The reconstruction condition decision part 302 stores the decided reconstruction condition in the memory 102.

Figure 5:
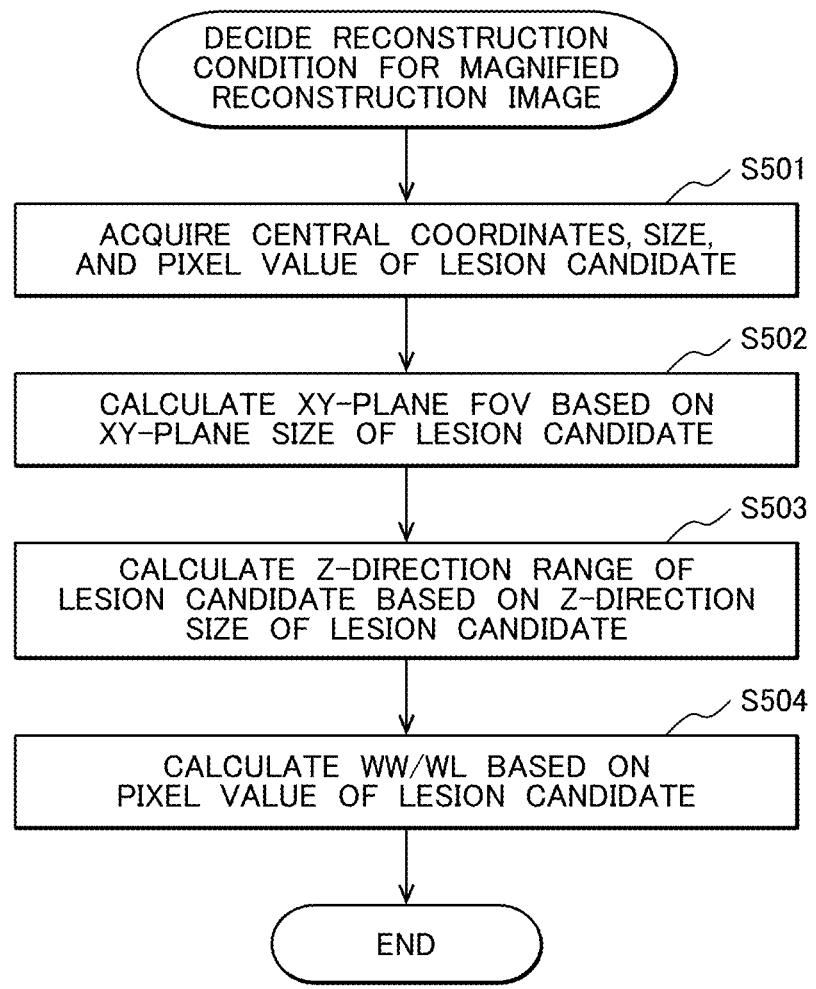
FIG. 5 is a flow chart showing an exemplary flow of processing of deciding a reconstruction condition for a magnified reconstruction image according to the first embodiment.

An example of a processing flow of this step is described with reference to FIG. 5.
(S501)
The reconstruction condition decision part 302 acquires data on central coordinates, size, and pixel value of the lesion candidate contained in the lesion candidate data 300.

Figure 6A:
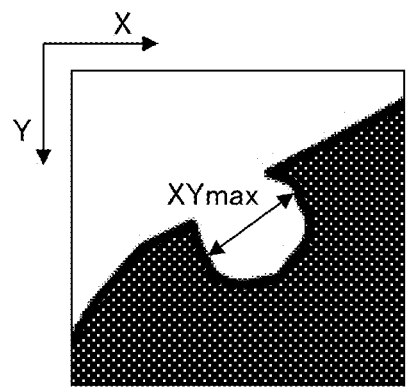
FIG. 6A to FIG. 6D are diagrams explaining the size of a lesion candidate and a pixel value.
Figure 6B:
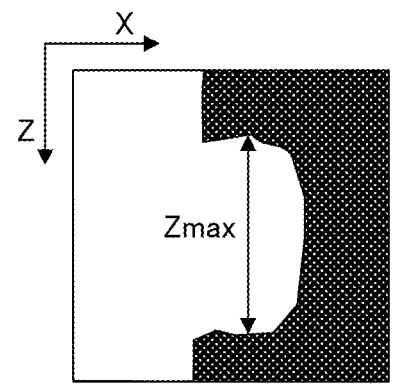
Figure 6C:
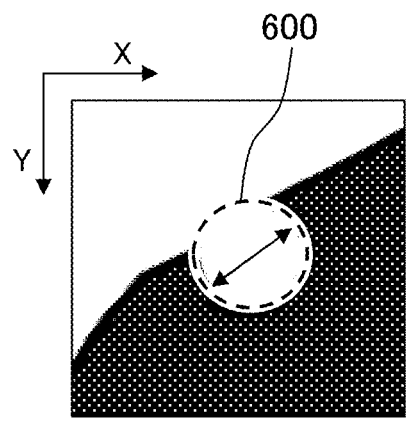
Figure 6D:
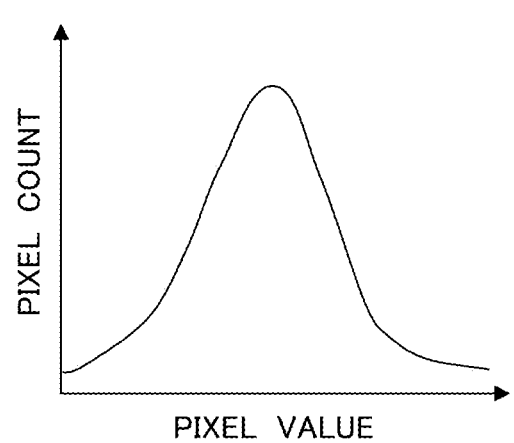

The size and pixel value of the lesion candidate are described with reference to FIG. 6. FIG. 6A shows an XY plane where a region including a lesion candidate is magnified, illustrating the maximum diameter XYmax of the lesion candidate on the XY plane. FIG. 6B shows a ZX plane where the region including the lesion candidate is magnified, illustrating the maximum diameter Zmax of the lesion candidate in the Z direction. FIG. 6C shows the XY plane where the region including the lesion candidate is magnified, illustrating a circle 600 having the maximum diameter XYmax. FIG. 6D is a graphical representation of a pixel value histogram in the circle 600 shown in FIG. 6C.

In this step, the maximum diameter XYmax of the lesion candidate on the XY plane or the maximum diameter Zmax of the lesion candidate in the Z direction, for example, is acquired as the data on the size of the lesion candidate. Further, a mode value, average or standard deviation of the pixel value as calculated from the pixel value histogram illustrated in FIG. 6D, for example, is acquired as the data on the pixel value of the lesion candidate.
(S502)
The reconstruction condition decision part 302 calculates a FOV (Field of View) on the XY plane of the magnified reconstruction image based on the maximum diameter XYmax on the XY plane of the lesion candidate, the maximum diameter acquired in S501. The following equation, for example, for example, is used for the calculation of the field of view FOV.

$$FOV = XY\mathrm{max} \times L \quad (1),$$

where "L" denotes a previously specified magnification ratio, e.g., 2.0. Alternatively, "FOV" may be fixed to a preset value while the value of "L" may be specified according to the value of XYmax.
(S503)
The reconstruction condition decision part 302 calculates a Z-direction range of the magnified reconstruction image based on the Z-direction maximum diameter Zmax of the lesion candidate acquired in S501. The following equation, for example, is used for the calculation of the Z-direction range.

$$PosA = z0 - (Z\mathrm{max} \times M)/2 \quad (2)$$

$$PosB = z0 + (Z\mathrm{max} \times M)/2 \quad (3),$$

where "PosA" and "PosB" denote a start position and an end position in the Z direction, respectively; "z0" denotes a central coordinate of the lesion candidate in the Z direction; and "M" denotes a previously specified magnification ratio, e.g., 2.0. Alternatively, the range from "PosA" to "PosB" may be fixed to a preset value while the value of "M" may be specified according to the value of "Zmax".

An interval "Int" between the magnified reconstruction images in the Z direction may be set to the minimum interval specified at the time of shooting the medical image. The thickness "Thick" of the magnified reconstruction image may be calculated using the following equation.

$$\mathrm{Thick} = k \times M \times \mathrm{Int} \quad (4),$$

where "k" denotes a previously specified magnification ratio, e.g., 1.0. Alternatively, "Thick" may be fixed to a preset value.

(S504)

The reconstruction condition decision part 302 calculates a window width WW and a window level WL based on the pixel value of the lesion candidate acquired in S501. "WW" and "WL" are included in display conditions for display of the magnified reconstruction image. As "WL", the mode value or average value of the pixel value calculated from the pixel value histogram as illustrated in FIG. 6D is used as "WL". The following equation is used for the calculation of "WW", for example.

$$WW = \text{range}(p \times SD \leq \text{range}),$$

$$P \times SD(p \times SD > \text{range}) \qquad (5),$$

where "range" denotes a lower limit of "WW"; "SD" denotes a standard deviation calculated from the pixel value histogram; and "p" denotes a preset coefficient, e.g., 3.0.

Figure 4:
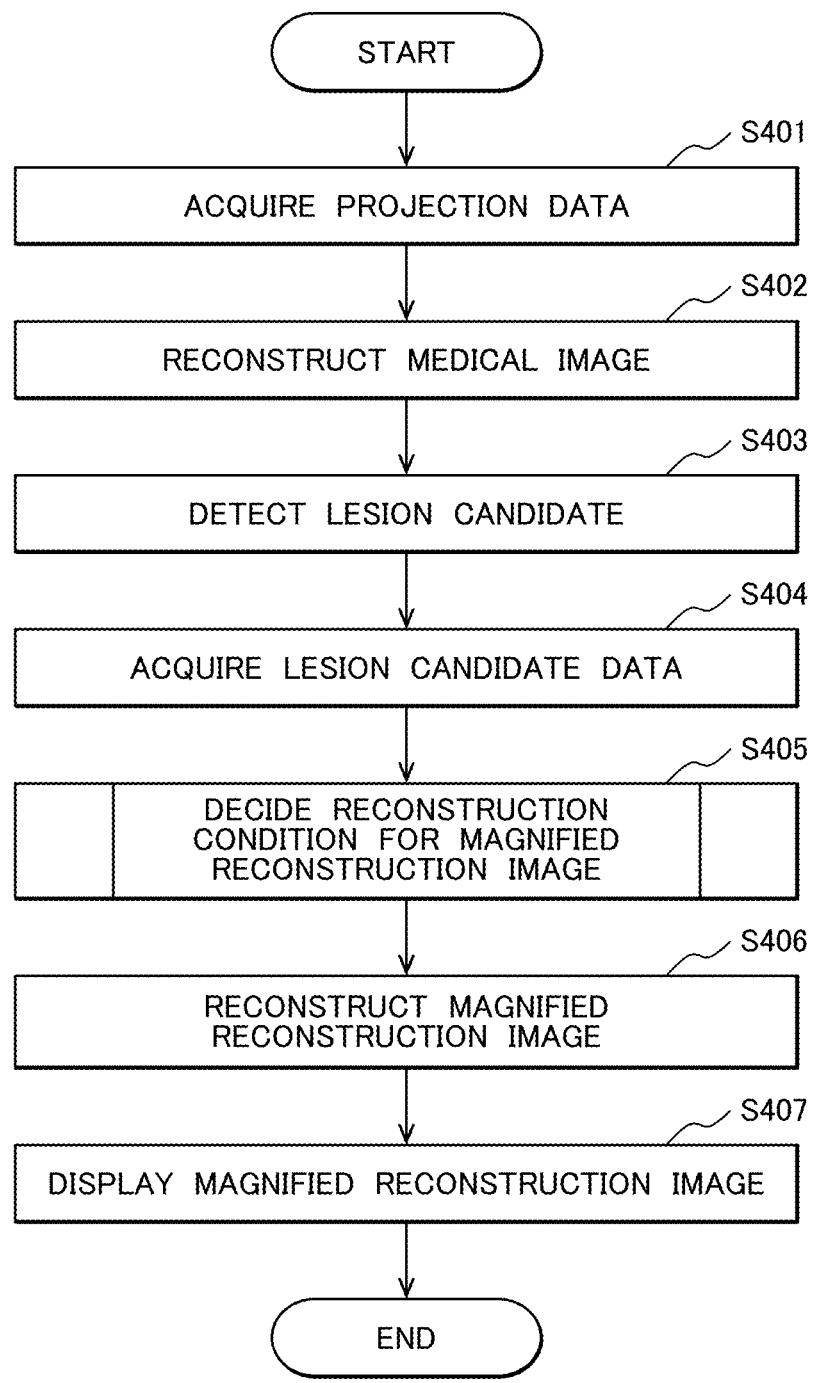
FIG. 4 is a flow chart showing an exemplary flow of processing of the first embodiment.

The description returns to FIG. 4.

(S406)

The magnification reconstruction part 303 acquires, from the memory 102, the reconstruction condition decided in S405. The magnification reconstruction part 303 reconstructs a magnified reconstruction image based on the reconstruction condition thus acquired. The magnified reconstruction image thus reconstructed may be transmitted to the medical image database 110 or the medical image interpretation device 111 via the network adaptor 104 and the network 108.

In a case where volume data of the subject is acquired by the medical image shooting device 109, the magnified reconstruction image includes not only the images on the XY-plane but also images on a YZ plane or on the ZX plane or oblique images taken at any cutting-plane angle.

(S407)

The magnified reconstruction image reconstructed in S406 is displayed on the display part 107.

Figure 7A:
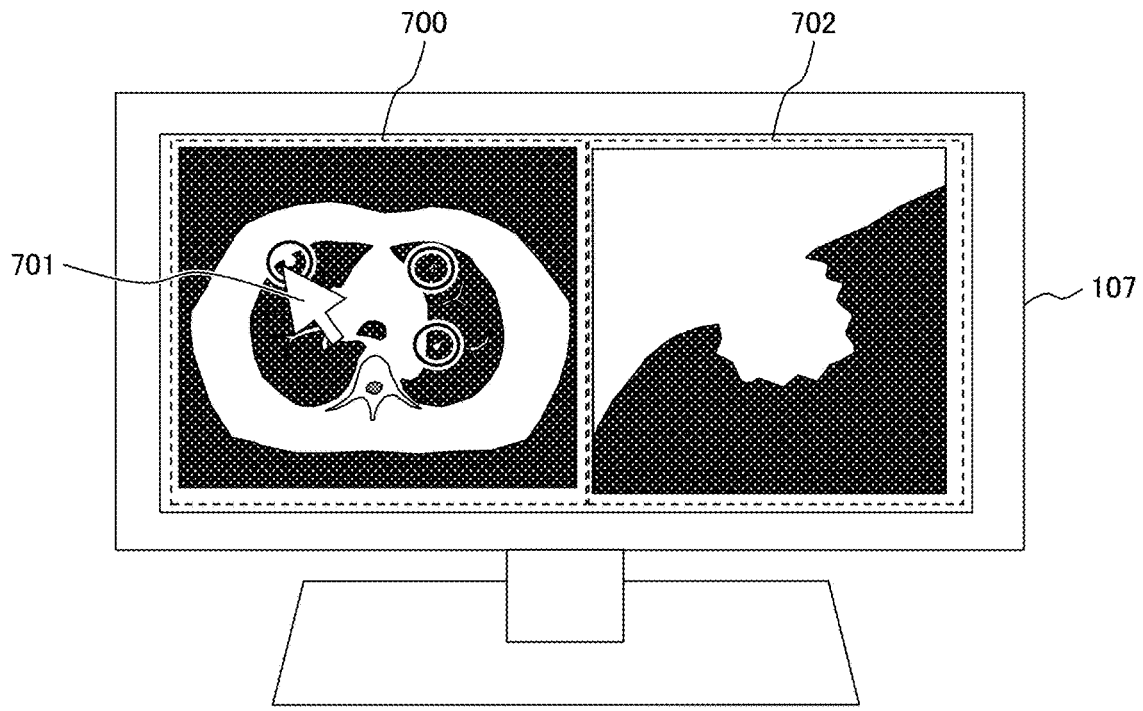
FIG. 7A and FIG. 7B each show an example of the magnified reconstruction image displayed on a screen.
Figure 7B:
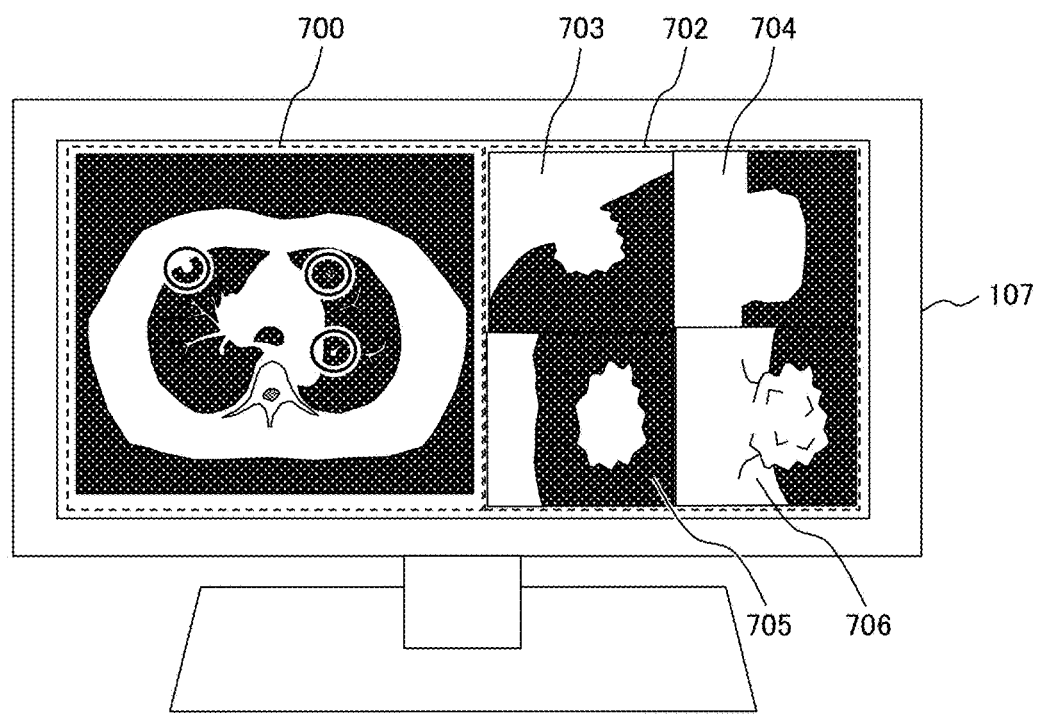

Display examples of the magnified reconstruction image are described with reference to FIG. 7. FIG. 7A shows an example where a magnified reconstruction image is displayed along with a medical image where lesion candidates are detected. FIG. 7B shows an example where multiple planar images of magnified reconstruction image and a three-dimensional image are displayed along with the medical image where the lesion candidates are detected.

In FIG. 7A, the medical image where the lesion candidates are detected is displayed on a lesion candidate display part 700 of the display part 107, allowing each of the lesion candidates to be selected by means of a mouse pointer 701. When the operator selects with the mouse pointer 701 a desired lesion candidate from among the lesion candidates displayed on the lesion candidate display part 700, a magnified reconstruction image of the selected lesion candidate is displayed on a magnified reconstruction image display part 702 of the display part 107. The magnified reconstruction image is displayed in response to the selection made by the operator whereby only a magnified reconstruction image of a lesion candidate which the medical image interpretation specialist as the operator wants to identify is displayed. Hence, time required for establishing the diagnosis of the lesion candidate can be reduced.

Before the reconstruction of the magnified reconstruction image, or before S405 in FIG. 4, for example, more than one lesion candidate is detected so that a desired lesion candidate may be selected from the medical image displayed on the display part 107. In this case, the use of capacity of the storage part 103 or the like can be reduced because the quantity of magnified reconstruction image to be reconstructed is limited.

In FIG. 7B, the medical image where the lesion candidate is detected is displayed on the lesion candidate display part 700. Multiple planar images such as an XY planar image 703, a ZX planar image 704, and a YZ planar image 705 and a three-dimensional image 706 are displayed on the magnified reconstruction image display part 702 as the magnified reconstruction images of the lesion candidates. Incidentally, an oblique image taken at any cutting-plane angle may be displayed in place of the three-dimensional image 706. The multiple planar images and the three-dimensional image are displayed so as to allow the operator to observe the lesion candidate multidirectionally. Hence, the time required for establishing the diagnosis can be reduced while greater accuracy of medical image interpretation can be achieved.

Here, description is made on a case where the medical image processing device 100 does not include the magnification reconstruction part 303 and the reconstruction part 113 of the medical image shooting device 109 performs the magnification reconstruction. Since the reconstruction involves a heavy processing load, high performance machine specification is required. It is therefore effective to use the existing reconstruction part 113 of the medical image shooting device 109 for executing the magnification reconstruction. Now referring to FIG. 4, changes made to the embodiment where the above-described medical image processing device 100 executes the magnification reconstruction are described below.

(S405)

Based on the lesion candidate data 300 acquired in S404, the reconstruction condition decision part 302 decides the reconstruction condition for the magnified reconstruction image. The reconstruction condition decision part 302 transmits the decided reconstruction condition to the medical image shooting device 109 via the network 108, so as to instruct the reconstruction part 113 to execute the reconstruction based on the relevant reconstruction condition.

(S406)

Upon receiving the reconstruction instruction, the reconstruction part 113 reconstructs a magnified reconstruction image based on the received reconstruction condition. As a response to the reconstruction instruction, the reconstruction part 113 transmits the resultant magnified reconstruction image to the medical image processing device 100.

As has been described, the medical image processing device 100 instructs the medical image shooting device 109 to execute the magnification reconstruction so that the medical image shooting device 109 can execute the magnification reconstruction. This provides for the utilization of the existing reconstruction part 113 of the medical image shooting device 109 so that the reconstruction load on the medical image processing device 100 is reduced. This also obviates the need for the high performance machine specification for the medical image processing device 100. Hence, the medical image processing device 100 can be constructed at low costs.

By the processing flow described above, the magnified reconstruction image of the lesion candidate detected by the medical image processing device 100 is displayed. Since the medical image interpretation specialist can check, along with the lesion candidate, the magnified reconstruction image as a specific data regarding the lesion candidate, time required for establishing the diagnosis of the lesion candidate can be reduced.

Second Embodiment

According to the description of the first embodiment, the magnification reconstruction condition for the magnified reconstruction image is decided on the basis of the size of the lesion candidate. The medical image processing device 100 is capable of calculating a malignant grade of a lesion candidate as well as detecting the lesion candidate. In this embodiment, description is made on how the reconstruction condition for the magnified reconstruction image is decided on the basis of the malignant grade of a lesion candidate. Since the overall structure and the processing flow of this embodiment are the same as those of the first embodiment, the description thereof is dispensed with.

An example of the processing flow of deciding the reconstruction condition for the magnified reconstruction image according to this embodiment is described with reference to FIG. 8.

(S801)

The reconstruction condition decision part 302 acquires a malignant grade along with the data on the central coordinates, size, and pixel value of the lesion candidate which are contained in the lesion candidate data 300. The data on the central coordinates, the size, and pixel value of the lesion candidate acquired in this step are the same as those of the first embodiment.

As for the malignant grade, a decimal number in the range of 0.0 to 1.0 is used as a numerical value indicating whether the lesion candidate is at a level of malignancy or not. Malignancy 0.0 indicates that the lesion candidate is benign, while malignancy 1.0 indicates that the lesion candidate is malignant. That is, when the malignancy is at 0.0 or 1.0, it is relatively easy to establish diagnosis. On the other hand, when the malignancy is in the vicinity of 0.5, it is relatively difficult to establish diagnosis which requires more specific data.

(S802)

The reconstruction condition decision part 302 calculates an FOV on the XY-plane of the magnified reconstruction image based on the on-XY-plane size and malignant grade of the lesion candidate acquired in S801. The following equation, a modification from the equation (1), for example, is used for the calculation of the field of view FOV.

$$FOV = XYmax \times L^{(1-|1-2R|)} \quad (6),$$

where "R" denotes the malignant grade, using a decimal number in the range of 0.0 to 1.0.

(S803)

The reconstruction condition decision part 302 calculates a Z-direction range of the magnified reconstruction image based on the Z-direction size and malignant grade of the lesion candidate acquired in S801. The following equations as modified from the equation (2) and the equation (3), for example, are used for the calculation of the Z-direction range.

$$PosA = z0 - (Zmax \times M^{(1-|1-2R|)})/2 \quad (7)$$

$$PosB = z0 + (Zmax \times M^{(1-|1-2R|)})/2 \quad (8),$$

Further, the interval "Int" between the magnified reconstruction images in the Z direction may be set to the minimum interval specified when the medical image is taken. The thickness "Thick" of the magnified reconstruction image may be calculated using the following equation, which is a modification of the equation (4).

$$Thick = k \times M^{(1-|1-2R|)} \times Int \quad (9)$$

(S804)

The reconstruction condition decision part 302 calculates a window width WW and a window level WL based on the pixel value of the lesion candidate acquired in S801. The calculation of WW and WL is performed in the same way as in S504 of FIG. 5.

(S805)

The reconstruction condition decision part 302 creates multiple planar images based on the malignant grade of the lesion candidate acquired in S801.

Figures 9A, 9B:
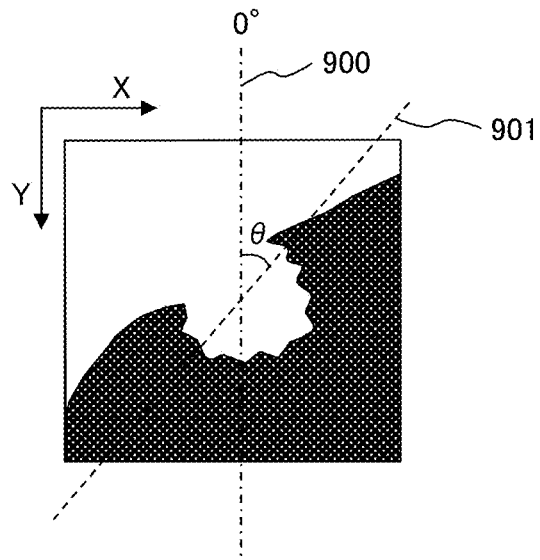
FIG. 9A and FIG. 9B are diagrams providing a supplementary explanation of processing of creating multiple planar images according to the second embodiment.

The creation of the multiple planar images is described with reference to FIG. 9. FIG. 9A shows an XY plane where a region including the lesion candidate is shown in enlarged dimension and where a reference line 900 and a gradient line 901 are shown. The reference line 900 passes through the center of the lesion candidate and extends in the Y direction. The gradient line 901 intersects the reference line 900 at the center of the lesion candidate and at an angle θ. The multiple planar images are formed along the gradient line 901. FIG. 9B shows an exemplary table illustrating a relation between the malignant grade R of the lesion candidate and the angle θ.

In this step, the angles θ of the multiple planar images are decided according to the malignant grade R of the lesion candidate. The reconstruction condition is decided such that the closer to 0.5 is the malignant grade, the more multiple planar images are created. That is, this step provides for more multidirectional observation of a lesion candidate which is relatively difficult to establish the diagnosis thereof.

Based on the reconstruction condition decided by the processing flow described above, the magnified reconstruction image of the lesion candidate is reconstructed and displayed. Since the medical image interpretation specialist can check the magnified reconstruction images as specific data on the lesion candidate along with the lesion candidate, time required for establishing the diagnosis of the lesion candidate can be reduced. In this embodiment, the field of view of the magnified reconstruction image and the angles of the multiple planar images are adjusted according to the malignant grade so that the more specific data is displayed for the lesion candidate, the diagnosis of which is more difficult to establish. Thus, the accuracy of the medical image interpretation can be increased.

Third Embodiment

As for the first and second embodiments, the description has been made on the reconstruction and display of the magnified reconstruction image. Some of the lesion candidates detected by the medical image processing device 100 may dictate the need for retake in order to acquire more specific data. In this embodiment, description is made on a process of deciding a retake condition based on the lesion candidate data. Since the overall structure of this embodiment is the same as that of the first embodiment, the description thereof is dispensed with.

A functional block diagram of this embodiment is described with reference to FIG. 10. These functions may be composed of dedicated hardware using ASIC (Application Specific Integrated Circuit), FPGA (Field-Programmable Gate Array) and the like, or otherwise, composed of software operating on the CPU 101. The following description is made on a case where the individual functions are composed of software. This embodiment includes the acquisition part 301 and a retake condition decision part 1002.

As in the first embodiment, the acquisition part 301 acquires the lesion candidate data 300.

The retake condition decision part 1002 decides the retake condition on the basis of the lesion candidate data 300.

An example of the processing flow of the embodiment is described with reference to FIG. 11.

(S1101)

The acquisition part 301 acquires the lesion candidate data 300 from the memory 102. The lesion candidate data 300 may be transmitted from the medical image processing device 100 via the network adaptor 104. Otherwise, data previously stored in the storage part 103 may be retrieved.

The lesion candidate data 300 acquired in this step may be limited to lesion candidate data 300 of a lesion candidate selected from a plurality of lesion candidates. A screen illustrated in FIG. 7A is used for selecting the lesion candidate data 300. The processing subsequent to this step is reduced by limiting the lesion candidate data 300 to a specific item, which results in the reduction of process time.

(S1102)

The retake condition decision part 1002 decides the retake condition on the basis of the lesion candidate data 300 acquired in S1101.

An example of the processing flow of this step is described with reference to FIG. 12.

(S1201)

The retake condition decision part 1002 acquires data on central coordinates, size, and pixel value of the lesion candidate contained in the lesion candidate data 300. In this step, the maximum diameter Zmax of the lesion candidate with respect to the Z direction, for example, is acquired as the data on the size of the lesion candidate. Further, an average value of the pixel values of the lesion candidate, a pixel value of a background of the lesion candidate, a contrast which is a difference between the pixel value of the lesion candidate and the pixel value of the background, or the like is acquired as the data on the pixel value of the lesion candidate.

(S1202)

The retake condition decision part 1002 calculates a shooting range in the Z direction based on the Z-direction maximum diameter Zmax of the lesion candidate, as acquired in S1201. The following equations (2) and (3), for example, are used for the calculation of the shooting range in the Z direction.

(S1203)

The retake condition decision part 1002 decides a shooting interval in the Z direction. The minimum interval of the medical image shooting device 109 is used as the shooting interval in the Z direction.

(S1204)

The retake condition decision part 1002 decides a tube current and a tube voltage on the basis of the data on the pixel value of the lesion candidate.

The description returns to FIG. 11.

(S1103)

The retake condition decided in S1102 is displayed on the display part 107.

(S1104)

A doctor as the operator checks for the retake condition along with the lesion candidate displayed on the display part 107 so as to determine whether or not to have a retake. In the case of retaking images, the processing flow proceeds to S1105. In the case of not having a retake, the processing flow ends.

(S1105)

The retake using the medical image shooting device 109 is performed based on the retake condition decided in S1102.

The retaken image permitting the observation of the details of the lesion candidate detected by the medical image processing device 100 is acquired and displayed by the flow of processing described above. Since the medical image interpretation specialist can check the retaken image as the specific data of the lesion candidate along with the lesion candidate, the time required for establishing the diagnosis of the lesion candidate can be reduced.

So far, a plurality of embodiments of the present invention have been described. The present invention is not limited to the embodiments as described above, but includes various modifications. For example, the embodiments are described in detail for readily understanding of the present invention which are not necessarily limited to the ones equipped with all structures as described above. It is possible to replace a part of the structure of one embodiment with the structure of another embodiment. The one embodiment may be provided with an additional structure of another embodiment. It is further possible to add, remove, and replace another structure to, from and with a part of the structure of the respective embodiments.

REFERENCE SIGNS LIST

100: medical image processing device, 101: CPU, 102: memory, 103: storage part, 104: network adaptor, 105: bus, 106: input part, 107: display part, 108: network, 109: medical image shooting device, 110: medical image database, 111: medical image interpretation device, 112: projection data acquisition part, 113: reconstruction part, 200: tomographic image, 201: lesion candidate, 300: lesion candidate data, 301: acquisition part, 302: reconstruction condition decision part, 303: magnification reconstruction part, 304: magnified reconstruction image, 600: circle, 700: lesion candidate display part, 701: mouse pointer, 702: magnified reconstruction image display part, 703: XY planar image, 704: ZX planar image, 705: YZ planar image, 706: three-dimensional image, 900: reference line, 901: gradient line

What is claimed is:

1. A diagnostic imaging support system including a medical image shooting device for shooting a medical image of a subject and a medical image processing device for processing the medical image, the system comprising:
   a projection data acquisition part for acquiring projection data of the subject;
   a reconstruction part for reconstructing the medical image based on the projection data;
   an acquisition part for acquiring lesion candidate data which is data of lesion candidates detected from the medical image;
   a reconstruction condition decision part for deciding, on the basis of the lesion candidate data, a reconstruction condition for a magnified reconstruction image which includes the lesion candidates and is more magnified than the medical image;
   a magnification reconstruction part for reconstructing the magnified reconstruction image by using the reconstruction condition; and
   a display part for displaying the magnified reconstruction image;
   wherein a display condition for the display part to display the magnified reconstruction image includes a window width and a window level and wherein the display condition is decided on the basis of a pixel value histogram contained in the lesion candidate data.

2. The diagnostic imaging support system according to claim 1, wherein the reconstruction condition includes a field of view, a reconstruction interval, and a thickness of the magnified reconstruction image.

3. The diagnostic imaging support system according to claim 1,
wherein the magnification reconstruction part creates a three-dimensional image including the lesion candidates, and
the display part displays the three-dimensional image along with the magnified reconstruction image.

4. The diagnostic imaging support system according to claim 1, wherein the display part includes a lesion candidate display part for displaying the lesion candidates along with the medical image, and when one of the lesion candidates displayed on the lesion candidate display part is selected, displays a magnified reconstruction image of the selected lesion candidate.

5. The diagnostic imaging support system according to claim 1, further comprising a retake condition decision part which decides, on the basis of the lesion candidate data, a retake condition as a condition for retaking the medical image.

6. A diagnostic imaging support system including a medical image shooting device for shooting a medical image of a subject and a medical image processing device for processing the medical image, the system comprising:
a projection data acquisition part for acquiring projection data of the subject;
a reconstruction part for reconstructing the medical image based on the projection data;
an acquisition part for acquiring lesion candidate data which is data of lesion candidates detected from the medical image;
a reconstruction condition decision part for deciding, on the basis of the lesion candidate data, a reconstruction condition for a magnified reconstruction image which includes the lesion candidates and is more magnified than the medical image;
wherein the reconstruction condition decision part decides the field of view of the magnified reconstruction image on the basis of sizes of the lesion candidates contained in the lesion candidate data, and wherein the reconstruction condition decision part adjusts the field of view of the magnified reconstruction image based on malignant grades of the lesion candidates contained in the lesion candidate data;
a magnification reconstruction part for reconstructing the magnified reconstruction image by using the reconstruction condition; and
a display part for displaying the magnified reconstruction image.

7. The diagnostic imaging support system according to claim 6, wherein the reconstruction condition includes a field of view, a reconstruction interval, and a thickness of the magnified reconstruction image.

8. The diagnostic imaging support system according to claim 6,
wherein the magnification reconstruction part creates a three-dimensional image including the lesion candidates, and
the display part displays the three-dimensional image along with the magnified reconstruction image.

9. The diagnostic imaging support system according to claim 6, wherein the display part includes a lesion candidate display part for displaying the lesion candidates along with the medical image, and when one of the lesion candidates displayed on the lesion candidate display part is selected, displays a magnified reconstruction image of the selected lesion candidate.

10. The diagnostic imaging support system according to claim 6, further comprising a retake condition decision part which decides, on the basis of the lesion candidate data, a retake condition as a condition for retaking the medical image.

11. A diagnostic imaging support system including a medical image shooting device for shooting a medical image of a subject and a medical image processing device for processing the medical image, the system comprising:
a projection data acquisition part for acquiring projection data of the subject;
a reconstruction part for reconstructing the medical image based on the projection data;
an acquisition part for acquiring lesion candidate data which is data of lesion candidates detected from the medical image;
a reconstruction condition decision part for deciding, on the basis of the lesion candidate data, a reconstruction condition for a magnified reconstruction image which includes the lesion candidates and is more magnified than the medical image;
a magnification reconstruction part for reconstructing the magnified reconstruction image by using the reconstruction condition, wherein the magnification reconstruction part reconstructs a second magnified reconstruction image at a different cutting-plane angle from that of the magnified reconstruction image, the second magnified reconstruction image including the lesion candidates and being more magnified than the medical image; and
a display part for displaying the magnified reconstruction image, wherein the display part displays the second magnified reconstruction image along with the magnified reconstruction image.

12. The diagnostic imaging support system according to claim 11, wherein the reconstruction condition decision part decides the cutting-plane angle of the second magnified reconstruction image on the basis of malignant grades of the lesion candidates contained in the lesion candidate data.

13. The diagnostic imaging support system according to claim 11, wherein the reconstruction condition includes a field of view, a reconstruction interval, and a thickness of the magnified reconstruction image.

14. The diagnostic imaging support system according to claim 11,
wherein the magnification reconstruction part creates a three-dimensional image including the lesion candidates, and
the display part displays the three-dimensional image along with the magnified reconstruction image.

15. The diagnostic imaging support system according to claim 11, wherein the display part includes a lesion candidate display part for displaying the lesion candidates along with the medical image, and when one of the lesion candidates displayed on the lesion candidate display part is selected, displays a magnified reconstruction image of the selected lesion candidate.

16. The diagnostic imaging support system according to claim 11, further comprising a retake condition decision part which decides, on the basis of the lesion candidate data, a retake condition as a condition for retaking the medical image.

17. A diagnostic imaging support system including a medical image shooting device for shooting a medical image of a subject and a medical image processing device for processing the medical image, the system comprising:
- a projection data acquisition part for acquiring projection data of the subject;
- a reconstruction part for reconstructing the medical image based on the projection data;
- an acquisition part for acquiring lesion candidate data which is data of lesion candidates detected from the medical image;
- a reconstruction condition decision part for deciding, on the basis of the lesion candidate data, a reconstruction condition for a magnified reconstruction image which includes the lesion candidates and is more magnified than the medical image;
- a magnification reconstruction part for reconstructing the magnified reconstruction image by using the reconstruction condition;
- a display part for displaying the magnified reconstruction image; and
- a retake condition decision part which decides, on the basis of the lesion candidate data, a retake condition as a condition for retaking the medical image; wherein
- the display part includes a lesion candidate display part for displaying the lesion candidates along with the medical image, and
- the retake condition decision part decides the retake condition on the basis of the lesion candidate data of a lesion candidate selected from the lesion candidates displayed on the lesion candidate display part.

18. The diagnostic imaging support system according to claim 17, wherein the reconstruction condition includes a field of view, a reconstruction interval, and a thickness of the magnified reconstruction image.

19. The diagnostic imaging support system according to claim 17,
wherein the magnification reconstruction part creates a three-dimensional image including the lesion candidates, and
the display part displays the three-dimensional image along with the magnified reconstruction image.

20. The diagnostic imaging support system according to claim 17, wherein the display part includes a lesion candidate display part for displaying the lesion candidates along with the medical image, and when one of the lesion candidates displayed on the lesion candidate display part is selected, displays a magnified reconstruction image of the selected lesion candidate.

21. The diagnostic imaging support system according to claim 17, further comprising a retake condition decision part which decides, on the basis of the lesion candidate data, a retake condition as a condition for retaking the medical image.

22. A diagnostic imaging support system including a medical image shooting device for shooting a medical image of a subject and a medical image processing device for processing the medical image, the system comprising:
- a projection data acquisition part for acquiring projection data of the subject;
- a reconstruction part for reconstructing the medical image based on the projection data;
- an acquisition part for acquiring lesion candidate data which is data of lesion candidates detected from the medical image;
- a reconstruction condition decision part for deciding, on the basis of the lesion candidate data, a reconstruction condition for a magnified reconstruction image which includes the lesion candidates and is more magnified than the medical image;
- a magnification reconstruction part for reconstructing the magnified reconstruction image by using the reconstruction condition; and
- a display part for displaying the magnified reconstruction image;
- wherein the medical image shooting device includes the reconstruction part,
- the medical image processing device includes the reconstruction condition decision part,
- the medical image shooting device transmits the reconstructed medical image to the medical image processing device,
- the reconstruction condition decision part of the medical image processing device decides the reconstruction condition on the basis of the lesion candidates detected from the received medical image, and transmits, to the medical image shooting device, the reconstruction condition and a reconstruction instruction based on the reconstruction condition, and
- upon receiving the instruction, the reconstruction part of the medical image shooting device creates a second reconstruction image by using the reconstruction condition and based on the projection data.

23. The diagnostic imaging support system according to claim 22, wherein the reconstruction condition includes a field of view, a reconstruction interval, and a thickness of the magnified reconstruction image.

24. The diagnostic imaging support system according to claim 22,
wherein the magnification reconstruction part creates a three-dimensional image including the lesion candidates, and
the display part displays the three-dimensional image along with the magnified reconstruction image.

25. The diagnostic imaging support system according to claim 22, wherein the display part includes a lesion candidate display part for displaying the lesion candidates along with the medical image, and when one of the lesion candidates displayed on the lesion candidate display part is selected, displays a magnified reconstruction image of the selected lesion candidate.

26. The diagnostic imaging support system according to claim 22, further comprising a retake condition decision part which decides, on the basis of the lesion candidate data, a retake condition as a condition for retaking the medical image.

* * * * *